United States Patent
Govari et al.

(10) Patent No.: US 10,893,935 B2
(45) Date of Patent: Jan. 19, 2021

(54) REDUCING BREAST IMPLANT WEIGHT USING CHEMICALLY PRODUCED FOAM FILLING

(71) Applicant: Biosense Webster (Israel) Ltd., Yokneam (IL)

(72) Inventors: Assaf Govari, Haifa (IL); Yehuda Algawi, Binyamina (IL); Ilya Sitnitsky, Nahariya (IL)

(73) Assignee: BIOSENSE WEBSTER (ISRAEL) LTD., Yokneam (IL)

(*) Notice: Subject to any disclaimer, the term of this patent is extended or adjusted under 35 U.S.C. 154(b) by 117 days.

(21) Appl. No.: 16/248,429

(22) Filed: Jan. 15, 2019

(65) Prior Publication Data
US 2019/0314144 A1   Oct. 17, 2019

Related U.S. Application Data

(60) Provisional application No. 62/658,896, filed on Apr. 17, 2018.

(51) Int. Cl.
| | | |
|---|---|---|
| *A61F 2/12* | (2006.01) | |
| *A61L 27/18* | (2006.01) | |
| *A61L 27/56* | (2006.01) | |
| *B29C 44/18* | (2006.01) | |
| *B29K 83/00* | (2006.01) | |
| *B29K 105/04* | (2006.01) | |
| *B29L 31/00* | (2006.01) | |

(52) U.S. Cl.
CPC .............. *A61F 2/12* (2013.01); *A61L 27/18* (2013.01); *A61L 27/56* (2013.01); *A61F 2240/001* (2013.01); *B29C 44/181* (2013.01); *B29K 2083/00* (2013.01); *B29K 2105/04* (2013.01); *B29L 2031/7532* (2013.01)

(58) Field of Classification Search
CPC ........................................................ A61F 2/12
USPC ........................................................ 623/7–8
See application file for complete search history.

(56) References Cited

U.S. PATENT DOCUMENTS

| | | | |
|---|---|---|---|
| 4,599,367 A | 8/1986 | Bauman et al. | |
| 4,767,794 A | 8/1988 | Modic et al. | |
| 5,658,330 A | 8/1997 | Carlisle et al. | |
| 9,339,371 B2 | 5/2016 | Dvir et al. | |
| 2010/0143652 A1* | 6/2010 | Stockton | A61K 8/8111 428/141 |
| 2010/0163192 A1* | 7/2010 | Medoff | C08L 63/00 162/5 |
| 2011/0029077 A1 | 2/2011 | Choi | |
| 2011/0184530 A1* | 7/2011 | Datta | A61L 27/48 623/23.72 |

(Continued)

FOREIGN PATENT DOCUMENTS

| | | |
|---|---|---|
| EP | 2550942 A1 | 1/2013 |
| WO | 2014039414 A1 | 3/2014 |
| WO | 2016108228 A1 | 7/2016 |

OTHER PUBLICATIONS

EP Search Report—EP 19169454 dated Sep. 18, 2019.

*Primary Examiner* — Suzette J Gherbi
(74) *Attorney, Agent, or Firm* — Eugene L. Szczecina, Jr.

(57) ABSTRACT

A method for manufacturing a breast implant including producing an elastic filler material including foam, by mixing a carbonate with a hydrolyzed silicone. A flexible shell, configured for implantation within a breast of a human subject, is filled with the elastic filler material.

8 Claims, 1 Drawing Sheet

(56) References Cited

U.S. PATENT DOCUMENTS

| | | | | |
|---|---|---|---|---|
| 2013/0289235 A1* | 10/2013 | Daniloff | ............... | A61L 31/16 |
| | | | | 528/372 |
| 2018/0280131 A1* | 10/2018 | Schuessler | ............. | A61L 27/50 |
| 2019/0314144 A1* | 10/2019 | Govari | ................... | A61L 27/18 |
| 2020/0078490 A1* | 3/2020 | Leimer | ................ | A61L 24/108 |
| 2020/0100893 A1* | 4/2020 | Kihara | .................. | A61L 27/18 |
| 2020/0113671 A1* | 4/2020 | Algawi | ................ | A61F 2/0077 |
| 2020/0129286 A1* | 4/2020 | Algawi | ................. | A61L 27/56 |

* cited by examiner

REDUCING BREAST IMPLANT WEIGHT USING CHEMICALLY PRODUCED FOAM FILLING

CROSS-REFERENCE TO RELATED APPLICATIONS

This application claims the benefit of U.S. Provisional Patent Application 62/658,896, filed Apr. 17, 2018, whose disclosure is incorporated herein by reference.

FIELD OF THE INVENTION

The present invention relates generally to medical implants, and particularly to breast implants.

BACKGROUND OF THE INVENTION

A breast implant is either inserted in a human breast or attached on the breast, e.g., in order to replace tissue that has been medically removed in an operation such as a mastectomy, or for cosmetic purposes. The purpose of the breast implant is to restore to the breast its external form, including its tactile feel and weight.

Various technologies were proposed in patent literature to form breast implants. For example, U.S. Pat. No. 5,658,330 describes a breast prosthesis for implantation beneath the skin. In an embodiment, the prosthesis has an outer elastic shell which encloses a biocompatible fluid and a silicone foam insert of unitary construction having the shape and approximate consistency of breast tissue. The foam insert occupies substantially the entire volume enclosed by the shell of the implantable prosthesis and consists of a foam body that is molded to the shape of the breast. The insert is of unitary construction and is made by (a) heating a mold to an appropriate temperature; (b) mixing air bubbles into a dispersion of uncured silicone; (c) injecting the bubble-laden, uncured silicone into the preheated mold; and (d) applying a vacuum until the foam insert cures.

As another example, U.S. Pat. No. 9,339,371 describes a prosthetic implant material for use in a prosthetic implant, comprising a gel and optionally a gas. In an embodiment, the filling material is a mixture of an unrestricted grade of Silicone gel and specially customized hollow glass microspheres filled with a gas.

U.S. Patent Application Publication 2011/0029077 describes a medical implant that includes porous silicon with bubbles of different sizes, and a silicon film enclosing the porous silicon. Also, the medical implant includes porous silicon balls with bubbles and a silicon film enclosing the porous silicon balls. Cushion and weight of the implant can be properly adjusted so as to maintain the cushion at a level similar to that of cellular cells of the human body and to shorten a recovery time. Plural grooves or through-holes are provided on a surface of the implant, and thus body fluid smoothly flows through the grooves or through-holes to improve the affinity of the implant against the cellular cells.

SUMMARY OF THE INVENTION

A method for manufacturing a breast implant including producing an elastic filler material including foam, by mixing a carbonate with a hydrolyzed silicone. A flexible shell, configured for implantation within a breast of a human subject, is filled with the elastic filler material.

In some embodiments, the method further includes homogenizing the foam by spinning the foam during or after mixing the hydrolyzed silicone and the carbonate.

In some embodiments, mixing the carbonate includes mixing sodium bicarbonate.

In an embodiment, mixing the carbonate with the hydrolyzed silicone includes mixing the hydrolyzed silicone and the carbonate with a catalyst.

In another embodiment, producing the elastic filler material includes producing a foam of silicone gel mixed with carbon dioxide bubbles.

In some embodiments, producing the elastic filler material includes tuning a hardness of the silicone gel by tuning at least one of a size and a density of the carbon dioxide bubbles.

There is additionally provided, in accordance with an embodiment of the present invention, a breast implant that includes an elastic filler material and a flexible shell. The elastic filler material includes a homogeneous foam of silicone gel mixed with carbon dioxide bubbles. The flexible shell contains the elastic filler material and is configured for implantation within a breast of a human subject.

The present invention will be more fully understood from the following detailed description of the embodiments thereof, taken together with the drawings in which:

DETAILED DESCRIPTION OF EMBODIMENTS

Overview

A breast implant may contain an elastic filler material, such as silicone gel, which is contained in a sealed flexible shell. A breast implant filled with such a material would be relatively heavy, and may cause discomfort to the wearer of the implant. To reduce the weight of the implant a gas such as air or carbon dioxide may be injected into the gel, to effectively form a foam and/or an emulsion. However, gas injection can be relatively complicated, and a simpler process would be useful.

Embodiments of the present invention that are described hereinafter provide an implantable device that is used as a breast implant. In some embodiments, a foam filling of the implant is produced by chemical reactions. In the description hereinafter foam and/or emulsion are collectively referred to as 'foam,' for brevity. For producing the foam, an embodiment the disclosed method uses the fact that the silicone gel is formed by hydrolysis of a silicone monomer, yielding hydrochloric acid (HCl) as a byproduct. A carbonate, such as sodium bicarbonate is added to the hydrolyzed mixture, and the carbonate reacts with the HCl to produce carbon dioxide bubbles (and common salt, NaCl). The mixture, with the bubbles may be spun to even out the bubbles in the gel.

In an embodiment, the implant elasticity is tuned during production by tuning the hardness of the manufactured silicone gel, such that an implant made with the softest silicone gel would weight about 70 percent of that made with the hardest silicone gel. In an embodiment, tuning the hardness of silicone gel is performed by tuning the size and/or density of the gas bubbles created in the gel. The hardness of gel may be determined in the development stage of the gel preparation process, for example by trial and error, and kept the same by a stable manufacturing process.

In some embodiments, an implant is provided, that by using a chemical process to produce the bubbles, comprises a highly homogeneous silicone gel.

The disclosed technique can simplify the formation of light breast implants, for example by eliminating manufacturing steps such as gas injection and sealing steps. Furthermore, the disclosed technique may simplify the manufacturing process of the silicone gel itself, for example, by avoiding additional processes such as the rinsing out the HCl byproduct. Thus, implementing the disclosed technique may increase the availability of light breast implants.

System Description

Figure 1:
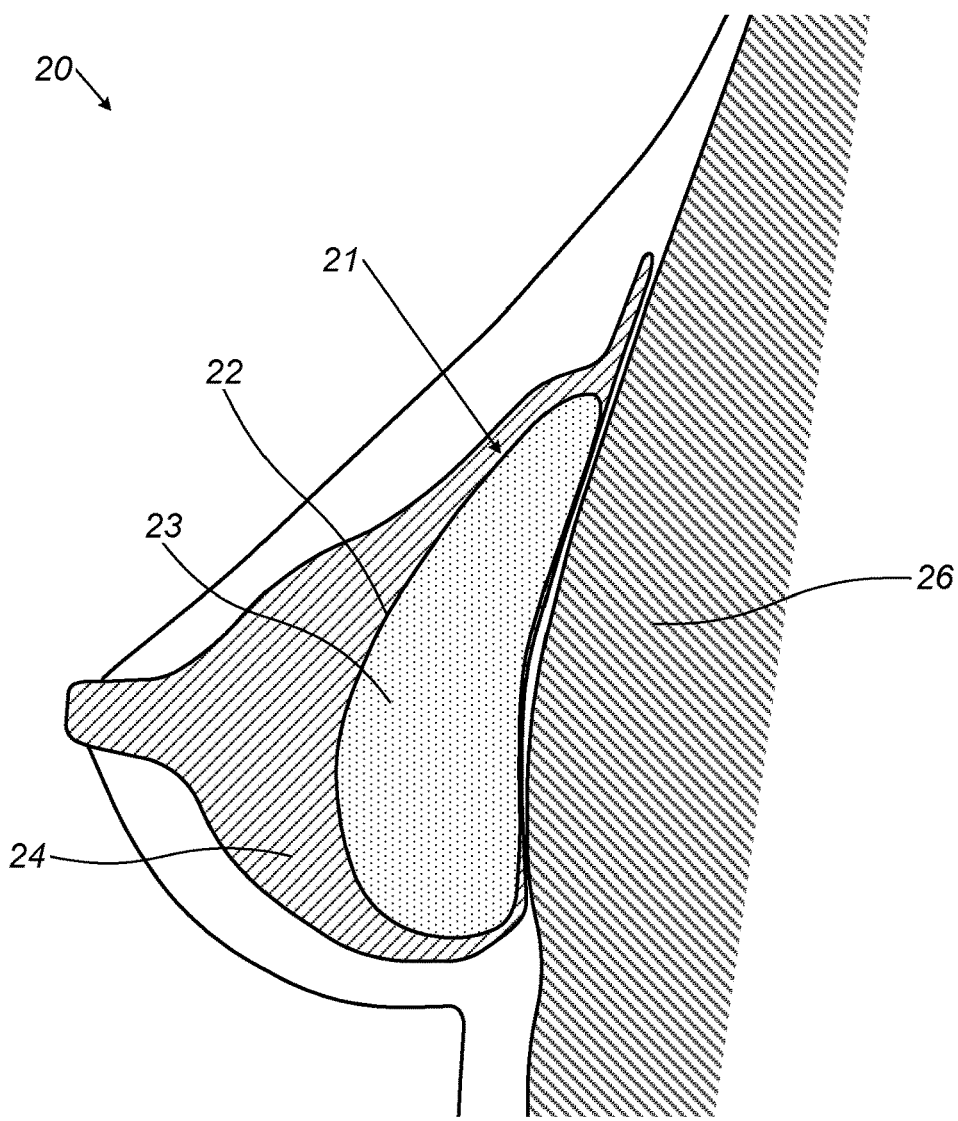
FIG. 1 is a schematic sectional illustration of a human female breast with a breast implant, in accordance with an embodiment of the invention.

FIG. 1 is a schematic sectional illustration of a human female breast 20 with a breast implant 21, in accordance with an embodiment of the present invention. Implant 21 comprises a shell 22 filled with a light weight foam 23, whereas the preparation of foam 23 is described in more detail below. In the disclosed embodiment, breast implant 21 is positioned as a subglandular implant between breast tissue 24 and a pectoralis major muscle 26. In alternative embodiments, breast implant 21 may be positioned either as a subfascial, subpectoral, or submuscular implant, referring to different positions of the implant relative to pectoralis major muscle 26, as will be understood by those skilled in the art. The example shown in FIG. 1 is chosen thus purely for the sake of conceptual clarity. Embodiments of the present invention may apply to any design of breast implant that contains a foam.

Reducing Breast Implant Weight Using Chemically Produced Foam Filling

Figure 2:
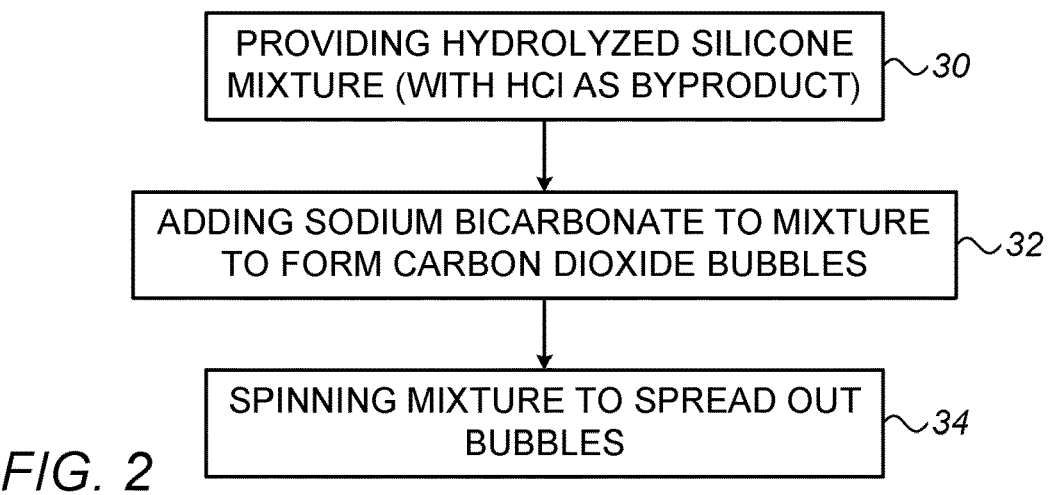
FIG. 2 is a flow chart that schematically illustrates a method for producing a foam filling for a breast implant, in accordance with an embodiment of the present invention.

FIG. 2 is a flow chart that schematically illustrates a method for producing foam filling 23, in accordance with an embodiment of the present invention. During part of the production stages of silicone gel, the hydrolyzed silicone contains hydrochloric acid (HCl). In some embodiments, a hydrolyzed silicone mixture with HCl as a byproduct is provided, at a preparation step 30. During one of the production steps, a carbonate, such as sodium bicarbonate (NaHCO$_3$) is added to the hydrolyzed mixture, in a carbonate addition step 32, and the carbonate reacts with the HCl to produce carbon dioxide bubbles (and common salt, NaCl):

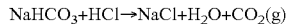

$$NaHCO_3 + HCl \rightarrow NaCl + H_2O + CO_2(g)$$

In some embodiments a catalyst may be added to the mixture to speed up the production of the bubbles at step 32 and/or the speed of curing of the resulting silicone-gel.

Finally, at a mixture homogenization step 34, the foam is put on a spinner which spins the mixture so as to even (i.e., homogenize) the spatial distribution of carbon dioxide bubbles in the foam.

In some embodiments, a flexible shell is filled with the filling material produced using the method of FIG. 2, and the shell is then sealed to produce breast implant 21.

The example flow chart shown in FIG. 2 is chosen purely for the sake of conceptual clarity. The quantities of chemicals and/or the conditions at which the chemical reaction produces the bubbles may vary, so as to tune the size and/or density of the chemically resulting gas bubbles in the gel, and the variation in size of bubbles.

As noted above, other chemicals may be used for creating the foam, where sodium bicarbonate was presented by way of example. Other manufacturing steps may be included, such as filtration and temperature settings, which for clarity are not shown. The timing of manufacturing steps may vary. For example, spinning of mixture can begin during or before or after production step 32.

Although the embodiments described herein mainly address breast implants, the methods and systems described herein can also be used in other applications, in which an implant comprising silicone-gel needs to be lightweight.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for manufacturing a breast implant, the method comprising:
    producing an elastic filler material comprising foam, by mixing a carbonate with a hydrolyzed silicone;
    homogenizing the foam by spinning the foam during or after mixing the hydrolyzed silicone and the carbonate; and
    filling a flexible shell, configured for implantation within a breast of a human subject, with the elastic filler material.

2. The method according to claim 1, wherein mixing the carbonate comprises mixing sodium bicarbonate.

3. The method according to claim 1, wherein mixing the carbonate with the hydrolyzed silicone comprises mixing the hydrolyzed silicone and the carbonate with a catalyst.

4. The method according to claim 1, wherein producing the elastic filler material comprises producing a foam of silicone gel mixed with carbon dioxide bubbles.

5. The method according to claim 4, wherein producing the elastic filler material comprises tuning a hardness of the silicone gel by tuning at least one of a size and a density of the carbon dioxide bubbles.

6. A breast implant, comprising:
    an elastic filler material comprising a homogeneous foam of silicone gel mixed with carbon dioxide bubbles; and
    a flexible shell, which contains the elastic filler material and is configured for implantation within a breast of a human subject.

7. A method for manufacturing a breast implant, the method comprising:
    producing an elastic filler material comprising foam, by mixing a carbonate with a hydrolyzed silicone;
    producing the foam of silicone gel mixed with carbon dioxide bubbles; and
    filling a flexible shell, configured for implantation within a breast of a human subject, with the elastic filler material.

8. The method according to claim 7, wherein producing the elastic filler material comprises tuning a hardness of the silicone gel by tuning at least one of a size and a density of the carbon dioxide bubbles.

* * * * *